United States Patent [19]

Petelenz et al.

[11] Patent Number: 4,752,285

[45] Date of Patent: Jun. 21, 1988

[54] METHODS AND APPARATUS FOR IONTOPHORESIS APPLICATION OF MEDICAMENTS

[75] Inventors: Tomasz J. Petelenz; Robert L. Stephen; Stephen C. Jacobsen, all of Salt Lake City, Utah

[73] Assignee: The University of Utah Research Foundation, Salt Lake City, Utah

[21] Appl. No.: 841,329

[22] Filed: Mar. 19, 1986

[51] Int. Cl.$^4$ ............................................. A61N 1/30
[52] U.S. Cl. ....................................... 604/20; 128/802
[58] Field of Search ................ 604/20, 891, 892, 896, 604/897; 128/798, 799, 802, 803

[56] References Cited

U.S. PATENT DOCUMENTS

| | | | |
|---|---|---|---|
| 3,991,755 | 11/1976 | Vernon et al. | 604/20 |
| 4,141,359 | 2/1979 | Jacobsen et al. | 128/172.1 |
| 4,166,457 | 9/1979 | Jacobsen et al. | 128/639 |
| 4,215,696 | 8/1980 | Bremer et al. | 128/803 |
| 4,250,878 | 2/1981 | Jacobsen et al. | 128/207.21 |
| 4,292,968 | 10/1981 | Ellis | 604/20 |
| 4,383,529 | 5/1983 | Webster | 604/20 |
| 4,416,274 | 11/1983 | Jacobsen et al. | 604/20 |
| 4,419,092 | 12/1983 | Jacobsen et al. | 604/20 |
| 4,465,074 | 8/1984 | Buchalter | 128/639 |
| 4,474,570 | 10/1984 | Ariura et al. | 604/20 |
| 4,477,971 | 10/1984 | Jacobsen et al. | 29/877 |
| 4,526,176 | 7/1985 | Bremer et al. | 128/803 |
| 4,557,723 | 12/1985 | Sibalis | 604/20 |
| 4,570,637 | 2/1986 | Gomes et al. | 128/803 |
| 4,602,909 | 7/1986 | Csillik et al. | 604/20 |
| 4,639,244 | 1/1987 | Rizk et al. | 604/151 |

OTHER PUBLICATIONS

Molitor et al., "Studies on Iontophoresis: I. Experimental Studies on the Causes and Prevention of Iontophoretic Burns," American Journal of Medical Science, vol. 198, pp. 778–785 (Dec. 1939).

Molitor, H., "Pharmacologic Aspects of Drug Administration by Ion-Transfer," The Merck Report, pp. 22–29 (Jan. 1943).

Abramowitz, "Ion Transfer or Iontophoresis," Galvanic Current, pp. 120–124.

Waud, D., "Iontophoretic Application of Drugs," Journal of Applied Physiology, vol. 23, pp. 128–130 (Jul. 1967).

Boone, D., "Hyaluronidase Iontophoresis," Physical Therapy, vol. 49, pp. 139–145 (1968).

Gore et al., "A Capacitive-Discharge, Microiontophoretic Device with Single-Ended Output," Journal of Applied Physiology, vol. 30, pp. 264–267 (Feb. 1971).

Spencer, H., "Programmable Nanoampere Constant Current Sources for Iontophoresis," Medical and Biological Engineering, vol. 9, pp. 693–702 (Nov. 1971).

Handbook of Physical Medicine and Rehabilitation, Second Edition, Krusen et al., editors, pp. 379–380 (1971).

(List continued on next page.)

Primary Examiner—C. Fred Rosenbaum
Assistant Examiner—Mario Costantino
Attorney, Agent, or Firm—Workman, Nydegger & Jensen

[57] ABSTRACT

Methods and apparatus for administering known quantities of medicaments by iontophoresis while avoiding burns caused by extremes in the pH of the medicament medium during passage of an electric current are disclosed. It has been found that, as iontophoresis progresses in conventional iontophoresis systems, the electrolysis of water occurs to produce hydrogen or hydroxyl ions at the interface of the electrode and medicament medium. Since these ions are highly mobile, they are transported directly into the skin of patient in preference to the larger medicament ions. Thus, extreme changes in pH are experienced which result in burns due to the acidification or alkalinization of the medicament medium and passage of electric current through the skin. The present invention also avoids the production of other competing ions by employing a reactive electrode. The electrode and the medicament are chosen such that the electrode will react with the complementary ion (the ion which forms upon the dissociation of the medicament in solution) to form an insoluble material.

40 Claims, 3 Drawing Sheets

OTHER PUBLICATIONS

Geller et al., "An Improved Constant Current Source for Microiontophoretic Drug Application Studies," Electroencephalography and Clinical Neurophysiology, vol. 33, pp. 430–432 (1972).

Bloom, F. E., "To Spritz or Not to Spritz: The Doubtful Value of Aimless Iontophoresis," Life Sciences, vol. 14, pp. 1819–1834.

Kahn, J., "Acetic Acid Iontophoresis for Calcium Deposits," Physical Therapy, vol. 57, pp. 658–659 (Jun. 1977).

Johnson et al., "On the Safe Electrical Administration of Ionized Drugs/Iontophoresis," 30th ACEMB. Los Angeles, Calif., (Nov. 5–9, 1977).

Painless Anesthesia Device Developed by U Researchers," Health Sciences Report, p. 5 (Jan. 1978).

Langley, "Iontophoresis to Aid in Releasing Tendon Adhesions," Physical Therapy, vol. 64, No. 9, p. 1395 (Sep. 1984).

Shaya et al., "Percutaneous Electrophoresis of Amino Acids and Urea," Medical and Biological Engineering and Computing, vol. 16, pp. 126–134 (1978).

"Iontophoresis," Medical Electronics, pp. 174 and 175 (Feb. 1984).

METHODS AND APPARATUS FOR IONTOPHORESIS APPLICATION OF MEDICAMENTS

BACKGROUND

1. Field of the Invention

This invention relates to methods and apparatus for administering substances by iontophoresis. More particularly, the present invention discloses methods and apparatus for administering determinable quantities of medicaments and the like by iontophoresis in a safe and efficient manner.

2. The Background of the Invention

The process of iontophoresis was reported as early as about 1740 for use in applying medication locally through a patient's skin and later in about 1900 for use in delivering medicaments to the eyes and ears. In its simplest terms, this technique involves the application of an electromotive force to drive ionic chemicals through the skin so that they can be absorbed by the adjacent tissues and blood vessels. By iontophoretic techniques, various substances (including some pharmaceuticals and medicaments) have been administered to a patient without the necessity of a hypodermic injection and without the associated problems, such as pain, the risk of infection, and trauma to the patient.

While iontophoresis has been the subject of continuous experimentation for many years, the process has not been used to any major extent by medical practitioners. Iontophoresis has been tested for use in treatments such as the application of local anesthetics, the application of medication for treatment of skin disorders, and the application of other limited types of medications in order to achieve a localized effect.

As mentioned above, iontophoresis involves the application of an electromotive force to drive ions through the skin. Accordingly, ions bearing a positive charge are driven into the skin at the anode of an electrical system, and ions bearing a negative charge are driven into the skin at the cathode of the electrical system. For example, positively charged ions such as zinc, copper, alkaloids, anesthetics, and certain vasodilating drugs are introduced into the skin or the mucous membranes from the positive pole. On the other hand, a negatively charged drug, such as salicylate, can be driven into the skin using the negative pole.

Some drugs have exhibited their effect at the site of iontophoresis, where they are initially introduced through the skin. Examples of such drugs which exhibit localized systemic effects upon iontophoresis through the skin are local anesthetics.

Various other drugs can be administered to exhibit systemic effects by iontophoretically driving the drug into the circulatory system. In such cases, the ions transferred through the skin are absorbed into the blood stream and enter the body's general blood circulatory system.

Iontophoretic delivery of medicaments can provide significant benefits over other methods of delivery. For example, when a medicament is taken orally, it must be absorbed through the digestive tract. However, uptake of the medicament through the digestive tract varies greatly from individual to individual. Moreover, the drug must pass through the liver where it is not unusual for upwards of 70% of the drug to be inactivated on the first pass through the liver. Thus, iontophoresis is capable of avoiding this "first pass effect" in the administration of certain medicaments. In addition, patient discomfort, noncompliance, and the risk of infection associated with injections are also eliminated when using iontophoresis.

While iontophoresis has been applied to many different drugs, it has never established itself as a widely used method for the delivery of medicaments. This was partly caused by the use of poor equipment and the lack of understanding of the mechanism of iontophoresis and its potential safety hazards. This historic view of iontophoresis, however, began to change somewhat in about 1959.

At that time, a test was devised, using iontophoresis, to diagnose cystic fibrosis. It was found that pilocarpine could be iontophoretically administered onto localized areas of skin so as to induce sweating. The sweat could then be collected and tested for abnormal levels of sodium or chloride, which is diagnostic of cystic fibrosis. This technique met with approval and was eventually selected by the Cystic Fibrosis Foundation as the standard and only acceptable test for diagnosing cystic fibrosis.

The widespread use of iontophoresis in diagnosing cystic fibrosis has resulted in some noticeable improvements in the equipment used to supply electrical current and in the electrodes used in iontophoretic applications. This use of iontophoresis has also led to some additional understanding of the mechanisms involved in iontophoresis. However, outside the field of cystic fibrosis diagnosis, the technique has yet to receive widespread acceptance.

Notwithstanding the limited acceptance of iontophoresis, the potential uses of iontophoresis can be readily appreciated from the previous discussion. Iontophoresis can obviously be used to introduce medicaments and other substances into the body without the necessity of an injection. Its use could thus become extremely significant in administering drugs and pharmaceuticals where frequent injections are required.

Frequent injections over a prolonged period of time as a form of treatment have several disadvantages. Many individuals find it difficult to adjust to the requirement of multiple daily injections, which are painful, carry the risk of infection, and cause additional strain on their already taxed system, possibly modifying the effects of the drug.

Iontophoresis as an alternative to existing methods of administration of medicaments has several advantages. The use of iontophoresis to administer such substances results in a high percentage of the substance actually reaching the systemic circulation—this is in direct contrast to oral administration where the drug is subject to the irregularities of the digestive process and possible inactivation by the liver prior to being absorbed into the systemic circulatory system. As a result, a relatively large quantity of a drug must be ingested orally in order to obtain the desired concentration of the drug in the bloodstream and to achieve the desired therapeutic effect. It will be appreciated that since each patient's digestive system functions differently, the amount of an orally ingested drug needed to achieve the desired therapeutic effect is often difficult to predict.

Another potential advantage of iontophoresis is the ability to administer medicaments over a sustained period of time without invasion of the body. Optimally, it is often desirable to maintain a certain constant level of medicament within the patient's system, instead of periodically injecting a bolus of medicament. However, due to limitations in the presently available iontophoresis systems, this sustained delivery is not practical because of the danger of electrical and chemical burns to the patient.

Another possible advantage of iontophoresis is the potential ability to deliver medicaments to a patient without also introducing sodium and other similar ions. Many medications exist as sodium salts, and solutions of these medications may contain a relatively large quantity of sodium which is an undesirable species for delivery to a patient who is suffering from cardiovascular or renal problems.

While the use of iontophoresis has many potential benefits, traditional iontophoretic techniques have suffered several drawbacks such that the iontophoretic administration of medicaments has not been generally very practical. In particular, traditional techniques for iontophoresis have been considered unsafe, unpredictable, inconvenient, or uneconomical. It is for these reasons that iontophoresis has not enjoyed widespread acceptance in the medical field. Moreover, due to the short duration of administration, iontophoresis has been almost exclusively used to administer locally active medicaments.

With respect to safety, it is found that iontophoresis may result in burns to the patient's skin. These burns stem from two sources: (1) galvanic sources where the electrical current itself causes burns, and (2) chemical sources where extremes in pH (which develop during the iontophoresis process) act in conjunction with electric current to result in chemical burns.

Methods and procedures have been developed to control serious galvanic burns and other electrical hazards. For example, it has been suggested that the electrical current used in the iontophoretic process be increased slowly and that limitations be placed on the amount of current delivered.

Galvanic burns can also be minimized or reduced by keeping the current density per unit area of skin below threshhold values at which burning begins. Low current densitites can be achieved by attention to techniques of iontophoresis, such as avoiding folds or wrinkles between the electrode and the skin (which cause high localized current density resulting in burns), using a gel-moistened electrode pad in connection with the electrode, and moistening the skin prior to and during iontophoresis. A further suggestion in the art has been to increase the surface area of the electrode so that the current is spread over a larger area, thereby reducing current density. See U.S. Pat. No. 4,416,274 (Jacobsen et al.) entitled "Ion Mobility Limiting Iontophoretic Bioelectrode," and U.S. Pat. No. 4,477,971 (Jacobsen et al.) entitled "Iontophoretic Electrode Structure."

It is more difficult to control pH and the resulting burns caused by extremes in the alkalinity or acidity of the medicament solution during passage of electric current. As the current passes between the electrode contact and the medium containing medicament, there is increased production of hydrogen ions ($H^+$) or hydroxide ions ($OH^-$). When the iontophoresis electrode is "inert," this increase in concentration is caused by the exchange of charge through the electrolysis of water.

Since the $H^+$ and $OH^-$ ions which result from the electrolysis of water are extremely mobile, they migrate rapidly through the solution away from the electrode and toward the skin of the patient. Thus, an area of extreme pH is ultimately created directly adjacent to the skin. This area of extreme pH is clearly dangerous and has been observed to cause serious burns when the current causes these ions to pass through the skin. Thus, the decrease changes in pH imposes a time limit on the duration of treatments, usually about twenty (20) to thirty (30) minutes.

Attempts have been made to control pH in the iontophoretic system. Heretofore, attempts are less than satisfactory. One method of attempting to control pH has been to introduce a buffer into the iontopheretic system. The introduction of buffers, however, is found to defeat some of the important useful features of iontophoresis.

The introduction of buffers results in increasing concentrations of additional ionic species within the system. In a solution containing a mixture of ions, the quantity of a specific ion that will be moved by a given electromotive force is proportional to (a) the concentration of the ion, (b) the mobility of the ion (lighter, less massive ions generally are more mobile), and (c) the valence charge on the ion.

Typically, the buffer ions which are usually small and very mobile (such as phosphate ions, and complementary cations such as sodium) will migrate through the solution at a much faster rate than will the larger ions (such as drug molecules) which are the medicament ions to be transported through the skin of the patient by the iontophoretic process. The result is that a large percentage of buffer ions may be driven into the skin by iontophoresis instead of the desirable medicament ions. Thus, the quantity of medicament molecules driven through the skin is seriously reduced and the quantity of undesirable ions driven through the skin is increased.

Moreover, as would be expected from the foregoing, the use of buffers aggravates the problem of quantification of the amount of medicament delivered in any given iontophoretic administration. If buffer ions are forced through the skin, it will be difficult or impossible to determine how much of the medicament has passed through the skin. This is particularly true since most medicament ions, especially drug ions, are larger, and slower in the electrical field created during the iontophoresis process than are the smaller buffer ions.

The existing literature has pointed out that administration of substances by ion transfer long has been regarded as one of the least accurate methods of administration. Indeed, the lack of accurate quantification techniques has been, and still is, one of the major objections to wide acceptance of iontophoresis.

A further problem encountered in the clinical use of iontophoresis is that iontophoresis systems have not been particularly convenient or economical. Generally, other methods of administration of medicaments have been less expensive and easier to use. Considerations of cost and convenience have, therefore, also impeded the general acceptance of iontophoresis.

As can be appreciated from the above discussion, the technique of iontophoresis has several major potential benefits for use in the medical area. Iontophoresis offers a technique whereby medicaments such as drugs may be introduced into the body noninvasively. That is, the patient may receive a needed medication without the necessity of an injection of a bolus of medicament and without the unknowns associated with the "first pass effect" of oral administration. Moreover, iontophoresis has the potential of providing a method whereby continuous, sustained doses of medications may be administered.

Despite this potential for iontophoretic administration techniques, the present state of iontophoresis is such that it is not particularly safe, since both galvanic and pH-induced burns are common. While galvanic burns can, to a certain extent, be controlled by appropriate techniques known in the art, pH-related burns associated with the passage of electrical current through the solution remain problematic. These burns are painful and difficult to heal.

In addition, existing methods and apparatus do not provide for adequate quantification of the medicament being administered. This is caused in large measure by the $H^+$ and $OH^-$ ions produced during iontophoresis. These highly mobile ions compete with the larger, less mobile medicament molecules for introduction in the patient, thereby resulting in an inability to determine how much of the medicament actually reaches the patient. At the same time, iontophoresis has not traditionally been particularly economical or convenient.

Thus, what is needed in the art is a technique for iontophoretically administering medicaments and other substances to the body in such a manner that burns and other safety hazards to the patient are avoided. It would be a significant advancement to provide improved methods and apparatus for administration of a medicament using iontophoresis which would allow the amount of the medicament administered to be better quantified, controlled, and delivered for prolonged time periods (i.e., over a period of hours or even days).

It would be a further significant advancement in the art to provide such methods and apparatus for administering medicaments by iontophoresis which could operate safely without the addition of buffering ions. It would also be a significant advancement in the art if methods and apparatus could be provided for iontophoretic administration of medicaments which provided for close control of pH within the system. It would be still another advancement in the art to provide methods and apparatus for administration of medicaments using iontophoresis which are economical and convenient to use. Such methods and apparatus are disclosed and claimed herein.

BRIEF SUMMARY AND OBJECTS OF THE INVENTION

The present invention is related to methods and apparatus for safely administering known quantities of medicaments (such as drugs, pharmaceuticals or other substances) to a patient using an iontophoretic process. As discussed above, iontophoresis essentially involves inducing an electrical current across a portion of a patient's body. This induced current causes ionic medicaments or other similar charged species to be transferred through the skin by the electromotive force. The present invention enables iontophoresis to occur while the pH of the solution is maintained within safe levels—levels where burns of the type encountered in the existing art are avoided. Furthermore, the iontophoretic techniques of the present invention maintain safe pH levels without the addition of buffering ions and minimize the formation of ions which compete with the ionic medicaments for transference through the skin, thereby inhibiting the quantification of the medicament being administered to the patient.

The present invention approaches the control of pH within the iontophoresis system by avoiding the formation of $H^+$ and $OH^-$ ions during iontophoresis, rather than by trapping or controlling the $H^+$ and $OH^-$ ions once they are produced. According to the present invention, it is possible to control the formation of $H^+$ and $OH^-$ ions within the system by maintaining the voltage at the interface of the electrode and the medicament solution (or other medium containing the medicament) below the electrolysis voltage of water.

The electrolysis reaction of water will occur at the positive electrode when the potential between the aqueous solution and the electrode exceeds approximately $+1.23$ volts versus a Standard Hydrogen Electrode (hereinafter sometimes referred to as "SHE"). Electrolysis of water occurs at the negative electrode when the potential between the aqueous solution and the electrode exceeds approximately 0.83 volts vs. SHE.

The direct consequence of the electrolysis of water at the positive electrode is the strong acidification of the medicament medium. Hydrogen ions are driven into the skin by the electromotive forces, thereby resulting in acid burns to the skin. The formation of $H^+$ ions, of course, is specific for the positively polarized anode, but a similar reaction occurs at the negative electrode, where the product of the reaction is the $OH^-$ ion which causes alkalinization of the medicament medium and yet more severe skin burns.

According to the preferred embodiment of the present invention, the formation of competing ions is minimized by providing an electrode for the iontophoresis system which reacts with ions which may be produced during iontophoresis in a specific manner. The electrode reacts to transfer charge in the solution at a voltage below the electrolysis voltages described earlier, so that the preferred reaction takes place and the voltage does not rise to where the unwanted electrolysis reaction can occur. Hence, the use of such a reactive electrode maintains the operating voltage at the interface of the electrode and the medicament medium below the voltage where electrolysis of water would occur (about $+1.23$ volts versus SHE at the interface of the anode with the medicament medium).

During iontophoresis, the medicament which exists in solution in the form of ions must necessarily be introduced into solution as a salt, base, or acid. It is preferable that the electrode adjacent the medicament solution reacts with ions complementary to the active medicament ion to form an insoluble precipitate at a voltage potential below the voltage potential of the electrolysis of water. This prevents such ions released as a result of the reaction at the electrode from competing with the medicament ions for transference through the skin during iontophoresis. (As used herein, the term "complementary ion" refers to the ion which forms the salt with the active medicament ion.) Through the use of such a reactive electrode and by controlling the voltage at the interface of the electrode and the medicament solution, it is possible to deliver iontophoretically quantifiable amounts of the medicament within safe pH levels.

An example of an iontophoresis system within the scope of the present invention utilizes a silver electrode at the anode and a solution containing complementary chloride ions so that silver chloride is formed. This system is useful when the system includes a drug which dissociates into a positive medicament ion and a negative chloride ion—the complementary ion. The silver chloride formed by the reaction of the complementary ion with the silver metal electrode is practically insoluble in water so that no additional competing ions (in this case, silver ions) are introduced into the system as the system operates to drive the medicament ions through the skin of the patient.

In addition, this reaction between the silver electrode and the complementary chloride ion occurs at a potential (i.e., 0.223 volts versus a SHE), measured at the interface between the electrode and the medicament medium, which is lower than the potential required for the electrolysis of water (i.e., +1.23 volts versus SHE). Thus, the production of H+ ions is avoided, and extremes in the pH of the medicament medium do not result. Thus, treatment time maybe markedly prolonged.

It is, therefore, a general object of the present invention to provide improved methods and apparatus for the use of iontophoresis which are safe and which allow the amount of the medicament introduced to a patient to be more accurately quantified.

Accordingly, it is an object of the present invention to provide improved methods and apparatus for the use of iontophoresis which provide for close control of the pH of the iontophoretic system to avoid burns caused by changes in pH concentration on or near the skin of the patient and to prolong treatment time during the iontophoresis process.

It is another object of the present invention to provide such an iontophoresis system which controls the pH of the medicament medium without the use of buffers.

Moreover, it is an object of the present invention to provide a iontophoresis system wherein the formation of competing ions is minimized so that the amount of the medicament administered remains proportional to the current flow.

It is also an object of the present invention to provide improved methods and apparatus for the use of iontophoresis which are both economical and simple and convenient to use.

These and other objects and advantages of the invention will become more fully apparent from the following description and appended claims.

DETAILED DESCRIPTION OF THE PREFERRED EMBODIMENTS

A. The Mechanism of Iontophoresis

As discussed above, iontophoresis is found to be a promising method of introducing medicaments, such as drugs and other similar substances, into a patient. In particular, iontophoresis provides for the efficient delivery of drugs without invading the body; however, in the past, iontophoresis has not been widely accepted because of the inability to produce a system which was safe, quantifiable, economical, and convenient.

One of the most serious problems prohibiting the widespread clinical use of iontophoresis is the production of painful burns on the skin of the patient after only a short period of iontophoresis. In existing iontophoretic systems, changes in the skin are typically observed within the first five minutes of iontophoresis, and burns often occur when the process continues for thirty minutes or more. These burns are difficult to heal and may not be fully manifest until after the treatment has been completed.

The more difficult type of burns to eliminate are burns caused by extreme changes in pH of the iontophoresed solution on or near the skin of the patient during passage of an electric current. In particular, electrical current flowing through an aqueous system, which would typically be used where a medicament is being iontophoresed into a patient, produces a large quantity of H+ or OH− ions, unless production of these ions is controlled. These ions (H+ or OH−) move rapidly in response to the electromotive forces existing within the iontophoresis system because of their large electrophoretic mobility. Thus, when these ions are produced in the iontophoresis process, they are rapidly driven into the patient's skin causing localized extremes in pH. Such localized extremes in pH result in burns on the skin of patients.

Figure 1:
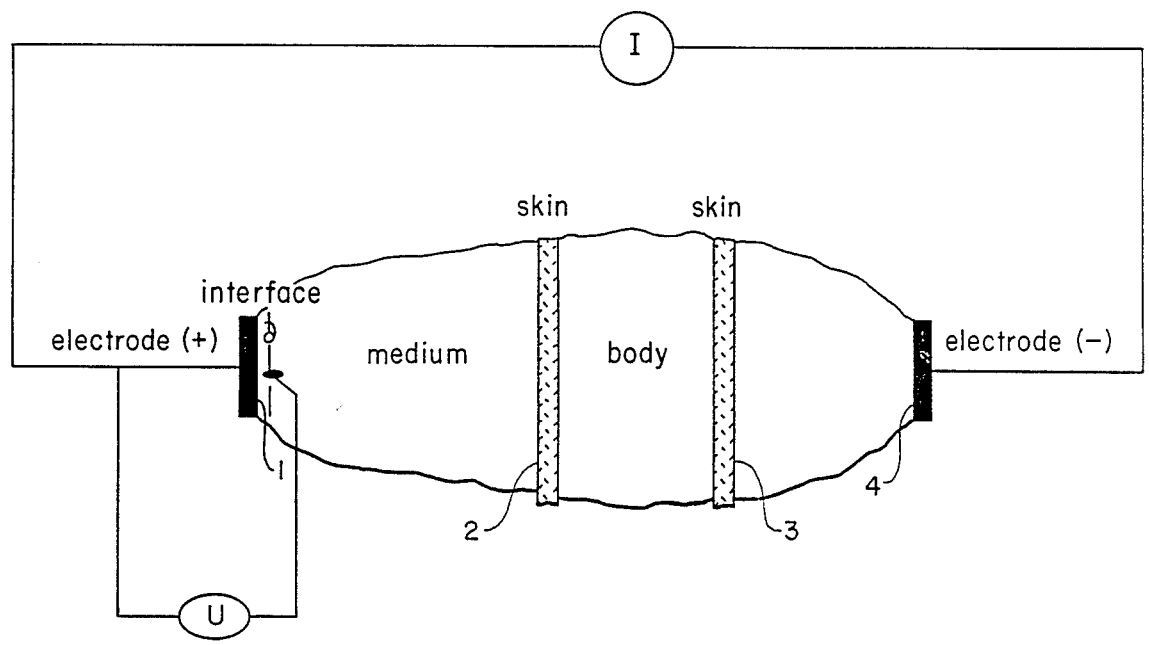
FIG. 1 is a schematic diagram of a general iontophoresis system which is within the scope of the present invention.

By definition, iontophoresis involves the transport of ions such as medicament ions, across a barrier such as the skin. The basic iontophoresis process can be clearly understood by reference to the schematic diagram of an iontophoretic system illustrated in FIG. 1. FIG. 1 illustrates the positive and negative electrode positioned on opposite sides of the body of the patient. Between the electrodes and the patient is a quantity of medium containing the desired medication. By this orientation, a series of interfaces is presented.

As seen in FIG. 1, these interfaces include the electrode-medicament medium interface between the anode and tha adjacent medicament medium (generally designated at 1), the medium-skin interface (generally designated at 2) between the medicament medium on the anode side of the system and the patient, a similar medium-skin interface on the cathode side (generally designated at 3), and finally the medium-cathode interface (generally designated at 4).

It will be appreciated that there will be a voltage differential across each of these interfaces, since each interface will present an additional resistance. Moreover, because voltge is inversely proportional to resistance, the additional resistance of each interface results in a greater voltage differential between the two electrodes. However, the total voltage drop across these interfaces is not necessarily directly related to the charge transfer in the system or the amount of medicament which is transferred to the patient. As will become evident, the amount of medicament transferred depends upon both the amount of current flow and the number and characteristics of the ions which compete with the medicament ion.

The present discussion will focus primarily on the electrode-medium interfaces. As discussed briefly above, it is necessary to control the voltage differential at these interfaces so that the electrolysis reaction of water does not occur at the electrode surface during iontophoresis. The mechanism for specifically preventing electrolysis of water by controlling the voltage differential at this interface is the subject of the following discussion.

B. Controlling Formation of H+ and OH− Ions

It will be appreciated that transportation of ions takes place in an electrical field such as that produced by the system illustrated in FIG. 1. Accordingly, the medicament to be delivered to the patient must exist in the system as an ion carrying an electrical charge. Since various compounds (such as salts, bases, or acids) dissociate upon dissolution in a solvent into two components, one positive and one negative, the medicaments used in iontophoresis are in the form of such compounds.

Thus, one of the components in the iontophoresis solution will be the active portion of the medicament and the other component will be the complementary ion. These charged ions are then subject to the electromotive forces exerted by the electrical field during iontophoresis such that the electrical field propels the ions through the system.

If the medicament to be administered to a patient exists in solution and is ionized, an external electrical field will cause the drug ions to be transported through the system. The ions will be attracted to the electrode having the opposite charge. This transportation of ions takes place in proportion to the product of the concentration, the mobility, and the charge (or valence) of the ions in solution. The fraction of total current carried by a particular ion species which determines the amount of transported drug, is called the transference number. The transference number for an ion K is expressed by Equation (1) which follows:

$$t_k = |z_k| \mu_k C_k / \Sigma(|z_i| \mu_i C_i) \quad (1)$$

where:
$z_k$ is the valence of ion K,
$\mu_k$ is the mobility of ion K,
$C_k$ is the concentration of ion K.

From Equation (1), it follows that the amount of transported drug, represented by ion K, decreases for every additional species in solution. As additional species are added to the system, the concentration of ion K is correspondingly reduced. Therefore, the use of buffers and the like to control pH is found to be unsatisfactory because of the addition of new species and the corresponding decrease in the concentration of the medicament.

In order to cause the medicament to move in the system at all, it is necessary to provide a driving force. In the case of iontophoresis, the driving force is an electrical potential difference. In order to cause current flow through the drug solution, it is necessary to provide a mechanism for charge exchange between the contact material of the electrode (typically a metal) and the electrolyte in the medium.

There are two types of electrodes which can be used for introducing a current through the iontophoresis system. These electrodes can generally be considered either "inert" or "reactive." An "inert" electrode, as defined herein is an electrode at which the charge is exchanged with the solution according to the reaction of electrolysis of water as represented in Equation (2):

$$2H_2O = O_2 + 4H^+ + 4e^- \quad (2)$$

at $V \geq 1.23$ V (at the positive pole) vs. SHE, where $e^-$ is the electron charge.

According to Equation (2), the electrolysis of water occurs if the voltage between the solution adjacent to the anode and the material of the anode exceeds approximately 1.23 volts vs. SHE. (It will be appreciated that the precise voltage for the electrolysis of water will be dependent upon the pH and the temperature of the solution, as well as certain other parameters; however, the value of +1.23 volts vs. SHE is used as a typical reference value which would be encountered under typical conditions.) It is particularly noteworthy that, in order to prevent the formation of H+ ions, it is the voltge at the interface of the electrode and the medicament medium which must be controlled and maintained below the electrolysis voltage of water.

The consequence of the reaction of Equation 2, as can be appreciated from the products of the reaction, is rapid acidification of the medium. The hydrogen ions produced are transported rapidly from the medium-electrode interface through the medium to the medium-skin interface, thereby resulting in acidification and contributing to burning of the skin.

While the above reaction is specific for the positively polarized electrode, it will be appreciated that a similar reaction takes place at the negative electrode where the product of the reaction is the hydroxyl ion. This reaction occurs at a voltage of approximately 0.83 volts (vs. a Standard Hydrogen Electrode) between the medium and the cathode. This, of course, creates alkalinization of the medium and tissues by the same general mechanism that acidification occurs at the positive electrode. The result, however, is the same since alkalinization can also cause burns to the patient during passage of an electric current.

The materials typically used in the art for the construction of iontophoretic electrodes function as "inert" electrodes, thereby conforming the reaction of Equation (2)—that is, the electrode causes the electrolysis of water as the iontophoresis procedure progresses. This obviously causes the introduction of small, fast ions (such as H+ and OH−) into the medium. These ions tend to carry a disproportionately large percentage of the total current in medium and thus impede the desired transportation of the medicament ions.

In addition, the evaluation of the transference numbers reveals that due to the introduction of H+ or OH− ions into the medium during iontophoresis, the fraction of the current transported by the medicament ions does not necessarily remain constant; in fact, the amount of current transported by the medicament ions may be significantly variable over time during iontophoresis. The consequence is that the actual rate of administration of the medicament to the patient will not remain constant over time. This is true even after correction for the appropriate transference number.

Thus, when electrolysis of water occurs in the iontophoresis medium, the increasing concentrations of H+ or OH− ions reduce the amount of drug transported through the skin of the patient. The result is that the dosage of the medicament delivered cannot be accurately quantified. Moreover, the potential treatment time is markedly reduced because of these factors.

C. The Reactive Electrode of the Present Invention

The iontophoresis system of the present invention in principle operates without the introduction or formation of additional ionic species (such as H+ ions or OH− ions or buffering ions) not related to the medicament ions and their complementary ions in solution. Since the addition of H+ or OH− ions to the system is adequately controlled, pH burns to the patient are avoided and the quantity of the medicament transported through the system remains more constant so that the amount of medicament administered is more accurately quantified, controlled, and prolonged.

It will be appreciated that even the presence of the complementary ion in the iontophoresis solution will compete with the transport of the medicament in through the skin of the patient. Thus, the preferred method of the present invention, which has been found to be suitable in avoiding extremes in pH during iontophoresis, utilizes an electrode which is capable of reacting with the complementary ion to form an insoluble precipitate at a voltage potential below the voltage potential of the electrolysis of water (that is, below approximately 1.23 volts vs. SHE at the positive electrode and approximately 0.83 volts vs. SHE at the negative electrode). The insoluble precipitate resulting from the reaction of the electrode with the complementary ion is practically insoluble in the medium and thus does not compete to any meaningful extent with the medicament ion.

An example of a presently preferred reactive electrode within the scope of the present invention is a silver anode used in combination with the chloride form of the medicament to be iontophoresed. The reaction of the silver electrode with the complementary ion is shown in Equation (3):

$$Ag + Cl^- \rightleftharpoons AgCl_{(solid)} + e^- \qquad (3)$$

at $V \geq 0.223$ V vs. SHE.

The resulting product (silver chloride) is a solid which precipitates out of solution.

As is evident from Equations (2) and (3), the silver electrode reacts with negative chloride ions to form silver chloride at a voltage (0.223 V vs. SHE) much less than the electrolysis voltage of water at the anode (1.23 V vs. SHE). Therefore, during iontophoresis, the silver electrode reacts with the chloride ions in the iontophoresis solution (which are formed by the dissociation of the medicament in the iontophoresis solution) at a voltage low enough to prevent formation of H+ ions in the iontophoresis solution.

With this system, it has been found that at the interface of the anode and the medicament solution, the voltage can be maintained relatively constant as long as there is sufficient metallic silver and chloride ions for the reaction to proceed to form silver chloride. This may be achieved by increasing the concentration of medicament and chloride ions in the medicament solution. With a high concentration of medicament and chloride ions, the reaction with metallic silver is favored over electrolysis of water, and the concentration of ionic species competing with medicament ions is minimized. Hence, the iontophoresed voltage will not climb during iontophoresis to the point that electrolysis of water and pH changes will occur.

As suggested above, it is desirable to remove the complementary ion from the iontophoresis solution so that it does not compete with the large medicament ion for transport of electric charge. Thus, the reaction of the electrode and the complementary ion preferably results in an insoluble precipitate or a species which is not mobile in the iontophoresis system as compared to the medicament ion.

In view of the foregoing, it will be appreciated that several features of the present invention are important to maintaining control over the pH of the iontophoresis solution, minimizing the amount of competing ionic species, and providing for more accurate quantification of the amount of medicament administered during iontophoresis.

First, the medicament must dissociate in the iontophoresis solution to form an active medicament ion and a complementary ion.

Second, the complementary ion (such as chloride ion) should preferably react with the adjacent electrode (such as a silver metal electrode) to produce an insoluble product (such as silver chloride) so that the complementary ion is isolated from the iontophoresis system. Since silver chloride is an insoluble precipitate in water, no additional ions are introduced into the system during iontophoresis which could compete with the transference of the medicament ion. The result is that the iontophoresis process favors the transportation of the medicament ion through the skin of the patient and the transportation is relatively proportional to the current flow.

It will also be appreciated that various types of electrodes may be practical for use in iontophoresis systems of the present invention. The most significant requirement for the electrode is that it and the nondrug complementary ion form an insoluble precipitate so that additional competing ionic species are not introduced into the iontophoresis solution.

Third, the reactive electrode and the complementary ion must be chosen such that a precipitate is formed at a voltage below the electrolysis voltage of water; that is, the reaction must take place at less than about 1.23 V vs. SHE at the anode. It will be appreciated that the reactive electrode may be either the anode or the cathode, depending on the particular needs of the iontophoresis system.

Fourth, by closely monitoring the voltage at the interface of the electrode and the adjacent medicament medium, it is possible to terminate the iontophoresis process before the electrolysis of water begins and the pH of the iontophoresis solution changes.

While monitoring the voltage at the interface of the electrode and the iontophoresis solution is valuable, it will be appreciated that, in practice, it may be cumbersome to monitor the voltage differential at this interface. If that voltage is monitored, iontophoresis can be continued with relatively little concern for chemical burns to the skin of a patient, as long as that voltage remains below the electrolysis voltage of water.

Alternatively, in order to avoid the need for continuously monitoring the voltage at the metal electrode-medicament solution interface, it is equally satisfactory to control the voltage indirectly by controlling the other factors which together can keep the voltage below the critical level. These factors include (a) providing sufficient amount of silver, (b) providing an excess of chloride ions in the medicament solution such that not all of the chloride ions can be consumed, (c) controlling the time of iontophoresis, and (d) the current of operation. It will be appreciated that providing an excess of chloride ions in the medicament solution will typically increase the concentration of medicament ions relative to any competing ions because the chloride ions will generally be added by adding to the medicament solution the hydrochloride form of the medicament. Since there is no substantial concentration of competing ions in the medicament solution, the maximum amount of medicament transported through the skin of the patient can be readily determined. Hence, by monitoring the current flow, iontophoresis can be continued for a time period within reasonably safe limits such that it can be assured that the pH of the solution does not drop because of the depletion of chloride ions in the medicament solution.

While the foregoing has referred to a silver electrode and chloride complementary ion system for illustrative purposes, other electrode and complementary ion combinations are possible. For example, a lead electrode and a sulfate complementary ion system is within the scope of the present invention. (It is acknowledged, however, that a lead electrode may not be acceptable under many circumstances because of the risk that lead may be transported into a patient.) In such a system, the lead electrode would form a lead sulfate precipitate at a potential below the potential for the electrolysis of water at the cathode. This results in the medicament ion being transported through the skin of the patient without significant changes in the pH of the electrolysis solution.

Figure 5:
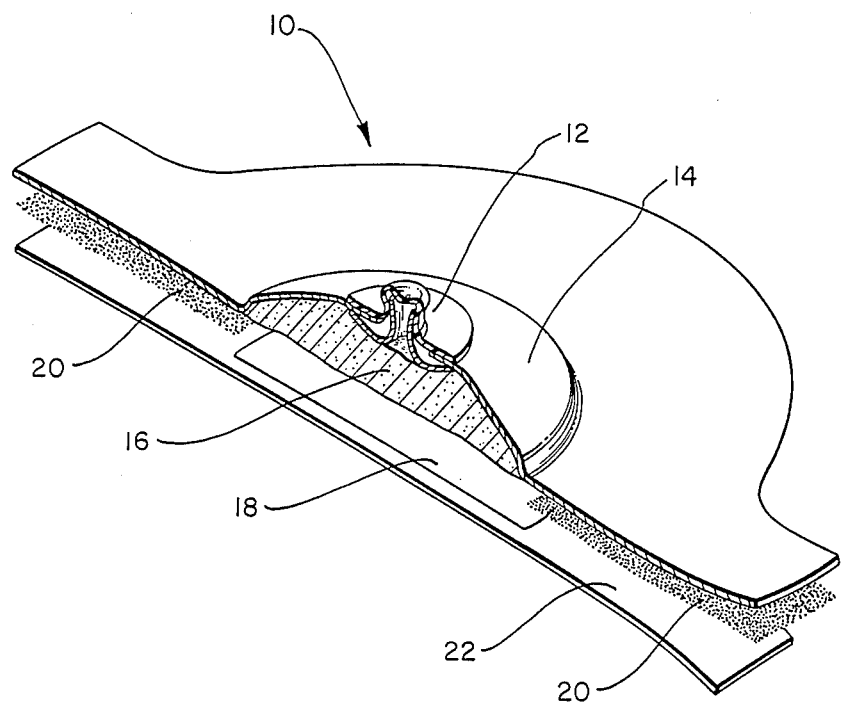
FIG. 5 is a cross-sectional exploded view of one embodiment of the present invention.

The use of the present invention can be better understood with reference to one embodiment of the present invention illustrated in FIG. 5. The iontophoresis apparatus, generally designated 10, includes electrode 12 and receptacle 14 for maintaining medicament medium 16 in communication with both the electrode and with the patient's body. Membrane 18 holds the medicament medium within the receptacle and adhesive 20 secures the apparatus on the patient's body. For convenience, release liner 22 covers the adhesive when the apparatus is not in use. The release liner can be easily removed to expose the adhesive prior to placing the apparatus on the patient's body.

Figure 6:
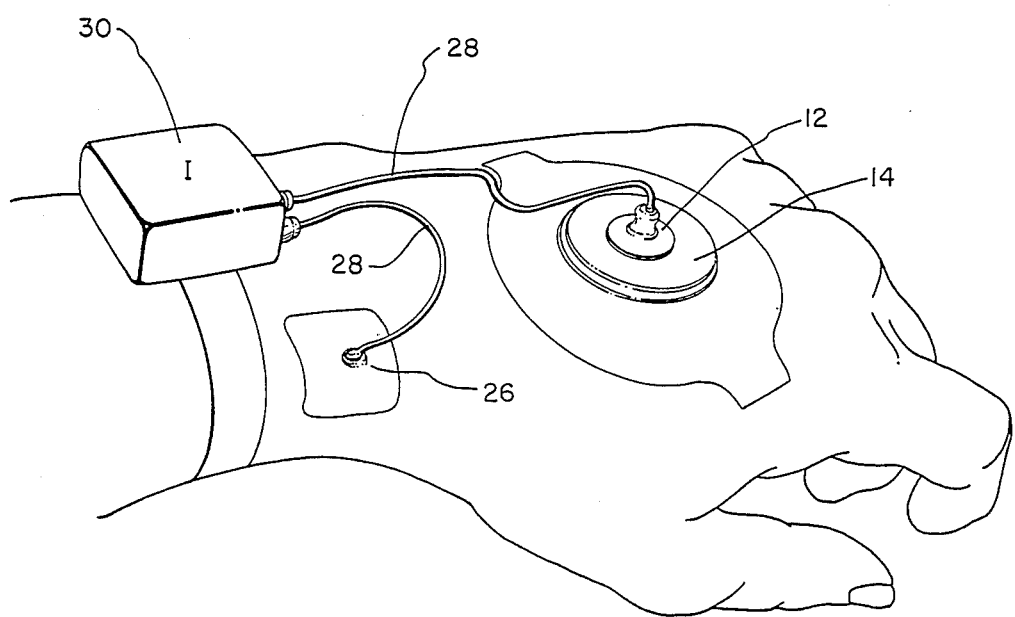
FIG. 6 is a perspective view of one embodiment of the present invention in use on a patient's body.

Referring now to FIG. 6, in use, the iontophoresis apparatus is placed on the patient's body and remote electrode 26 is placed a short distance away from the iontophoresis apparatus. Wires 28 running from current source 30 are attached to both the iontophoresis apparatus and the remote electrode.

D. Iontophoresis of Morphine By the Preferred Embodiment

The principles of the present invention, as well as its advantages, can be further understood by comparing the prior art iontophoresis of morphine with the iontophoresis of morphine using the reactive electrode of the present invention.

Figure 2:
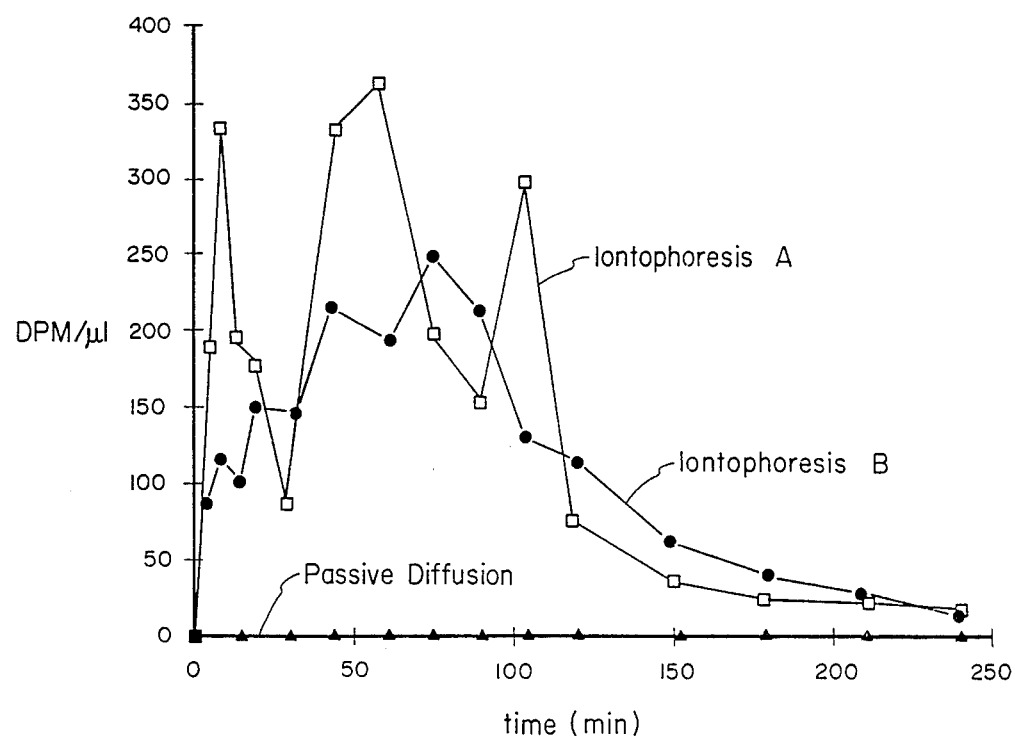
FIG. 2 is a graphical representation of data resulting from the iontophoresis of morphine through isolated rat skin flaps wherein a process within the scope of the present invention was utilized.

FIG. 2 illustrates the results of three tests which were conducted in order to determine the extent of transference of morphine through an isolated rat skin flap by passive diffusion and by iontophoresis using the reactive electrode. Utilizing known techniques, an isolated rat skin flap was prepared. A solution of radio-labelled morphine hydrochloride having a concentration of approximately 6 mg/ml was placed on one surface of the skin flap in order to determine the amount of morphine that would passively diffuse through the skin flap.

The amount of radio-labelled morphine which diffused through the skin flap was measured in blood collected from veins draining from the opposite side of the rat skin flap by detecting the number of disintegrations per minute per microliter of blood (DPM/$\mu$l). As is illustrated in FIG. 2, no significant amount of morphine passively diffused through the skin flap even after four hours.

By contrast, a significant amount of the radio-labelled morphine was absorbed into the blood after it was iontophoresed through the isolated rat skin flap using the techniques of the present invention. In two separate tests (the results of which are plotted in FIG. 2 as A and B), morphine hydrochloride in a concentration of approximately 6 mg/ml was iontophoresed through the isolated skin flap at a current of 0.5 mA for a period of sixty minutes using a silver metal electrode.

In an aqueous solution, morphine hydrochloride dissociates into a positively charged morphine ion and a negatively charged chloride. At a voltage of 0.23 V vs. SHE (or 0.0 V vs. Ag/AgCl electrode), the chloride ion reacts with metallic silver to form a silver chloride precipitate. This reaction is represented by the following chemical equation:

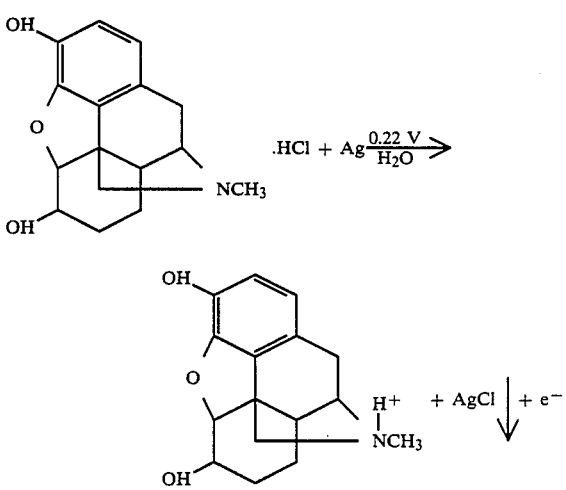

Using this mechanism, it will be appreciated that if a low voltage is maintained (i.e., below the electrolysis voltage of water), the morphine hydrochloride can react with a silver metal electrode to form an insoluble silver chloride precipitate, a morphine ion, and an electron. The result is that the morphine ion is transported through the aqueous solution, through the solution-skin interface, and then through the skin without the production of any undesirable complementary ionic species within the aqueous solution which would compete with the transport of the morphine ion.

Referring again to the results of the tests illustrated in FIG. 2, it will be appreciated that significant amounts of morphine hydrochloride passes through the isolated skin flap and were absorbed in the blood as a result of the iontophoresis. In addition, it is noteworthy that the pH of the morphine hydrochloride solution was about 6.0 at the beginning of the iontophoresis process in both tests A and B, and that the pH after sixty minutes of iontophoresis was still at about 6.0. Thus, despite the fact that iontophoresis was conducted for a period of sixty minutes, there was not the production of hydrogen ions which would change the pH and result in burns to the patient. As is discussed below, this is in sharp contrast to the situation where morphine is iontophoresed using conventional techniques.

In a separate series of tests, morphine sulfate was administered to human volunteers using a standard iontophoresis electrode (model No. EL500 available from Motion Control, Inc., Salt Lake City, Utah), A volume of 3 ml of morphine sulfate having a concentration of 10 mg/ml was iontophoresed into five patients at a current of 2 mA for a period of twenty minutes. The average concentration of the free plasma morphine (measured in nanograms per milliliter (ng/ml)) in blood taken from these patients at ten minute intervals is graphically represented by line A in FIG. 3. (Line A represents the average free plasma morphine amount, and the range of standard deviation for each measurement is indicated by the vertical arrows.)

At the beginning of the iontophoresis procedure, the pH of the morphine sulfate solution was 5.5; however, within twenty minutes, the pH had, on the average, fallen to the value of 2.0. As a result, iontophoresis had to be terminated after only twenty minutes in order to prevent significant burns to the patients. Even then, significant irritation and some burning resulted to the skin of the patients.

Unfortunately, the amount of morphine which was iontophoresed through the skin in this test was insufficient to achieve the analgesic effects desired. In an attempt to administer a greater amount of morphine to the patient, a second series of experiments were conducted using two electrodes containing morphine sulfate.

This second set of tests was conducted with five patients under the same conditions described above (with respect to the results plotted as Line A in FIG. 3), except that two separate sets of electrodes were simultaneously used with two separate current supplies at different skin locations on the patients so that the dosage could be increased. The average free plasma morphine amounts in blood samples taken from the patients at ten minute intervals is graphically represented as Line B in FIG. 3 (and the range of the standard deviation for each measurement is indicated by the vertical arrows.)

Figure 3:
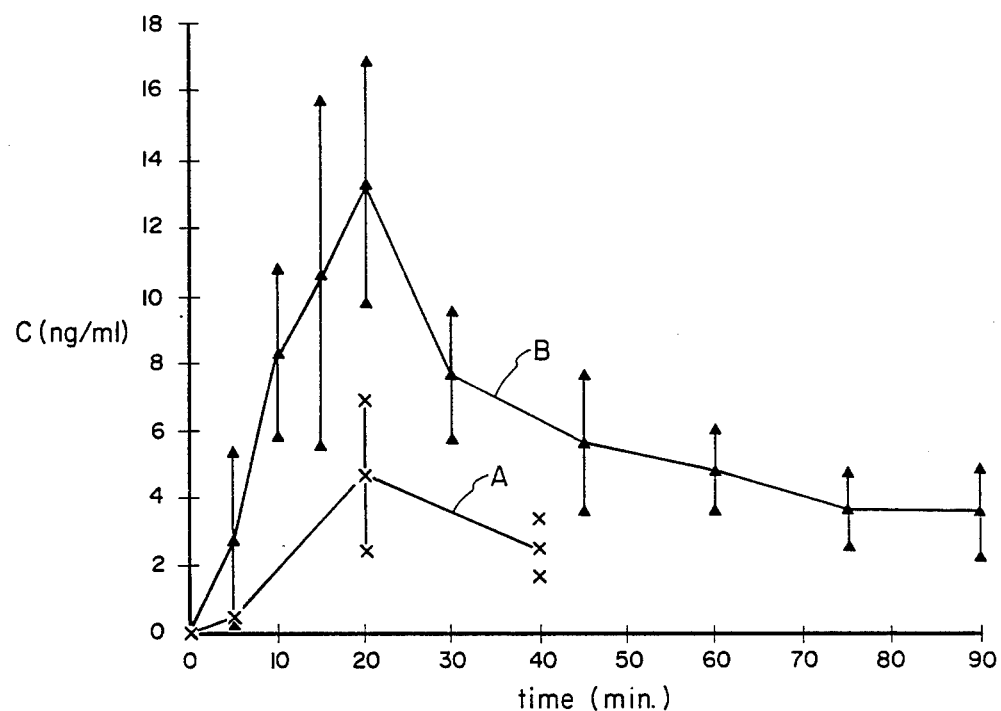
FIG. 3 is a graphical representation of data resulting from the iontophoresis of morphine in human volunteers where standard prior art techniques are utilized.

From Line B of FIG. 3, it is seen that upwards of 14 ng/ml of free plasma morphine was measured in the blood after twenty minutes of iontophoresis. The pH of the morphine sulfate during that period of iontophoresis also fell from about 5.5 to about 2.0, thus requiring the termination of the iontophoresis process.

Figure 4:
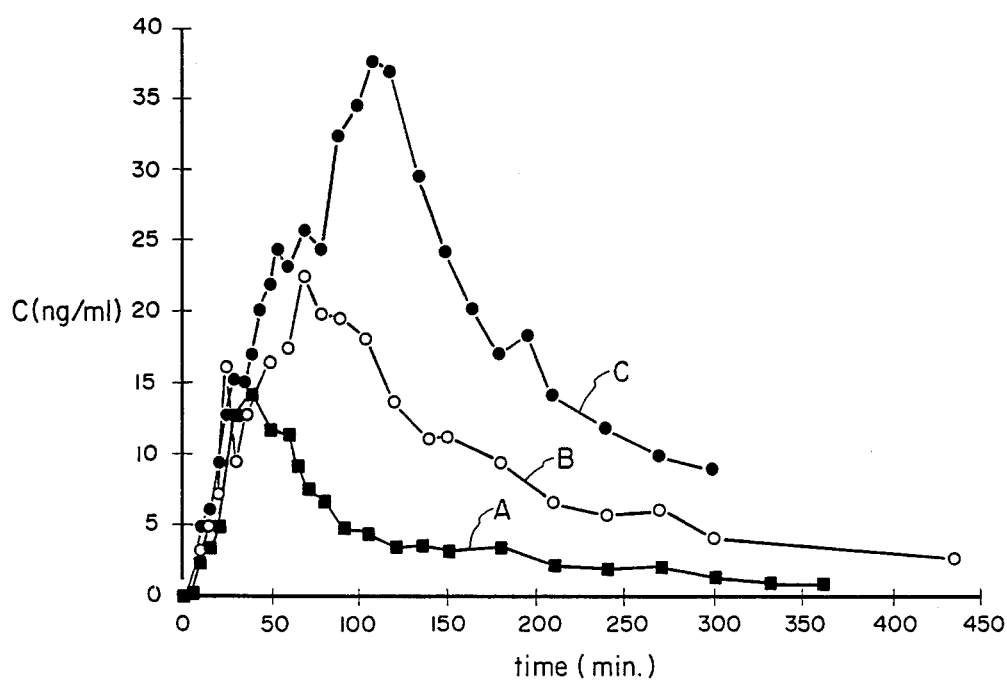
FIG. 4 is a graphical representation of data resulting from the iontophoresis of morphine in human volunteers wherein processes within the scope of the present invention were utilized.

In comparison to the data of FIG. 3, curve A of FIG. 4 graphically represents the results of iontophoresis of morphine hydrochloride according to the present invention. A silver electrode was used to administer morphine hydrochloride in aqueous solution having a concentration of 2 mg/ml. This solution was placed between the silver electrode and the surface of the skin of a human volunteer. Iontophoresis was performed at a current of 2 mA for sixty minutes. The amount of free plasma morphine measured in the blood of the volunteer at regular intervals is illustrated by Line A in FIG. 4.

As is clearly shown, significant amounts of the morphine were transported through the skin to the bloodstream of the patient during iontophoresis, and the residual concentration of the morphine in the blood continued for a significant time period after termination of iontophoresis. The fact that significant amounts of morphine were transferred by this process is indicated by a significant increase in the AUC. (Under certain conditions, the "Area Under the Curve" is proportional to the delivered dosage of the medicament.) Equally important, the initial pH of the morphine hydrochloride was about 6.1, and the pH was still about 5.5 after sixty minutes of iontophoresis. This change in pH is clearly within an acceptable range and is not significant enough to cause burns or require termination of iontophoresis.

A second test was run on a human volunteer under substantially the same conditions as indicated above, except that the concentration of the morphine hydrochloride in the aqueous solution was about 10 mg/ml and the iontophoresis time was ninety minutes. The results of the blood studies from the volunteer are graphically illustrated by Line B in FIG. 4.

After ninety minutes of iontophoresis, the pH was about 6.0, as compared to an initial pH prior to iontophoresis of about 6.1. Since there was essentially no change in the pH, no burning resulted and it was possible to continue the iontophoresis process for the ninety minute period without any adverse results. Moreover, significant amounts of the morphine were transferred through the skin by the iontophoresis process and absorbed into the bloodstream of the patients. The AUC (of Line B in FIG. 4) is 3588 ng-min/ml.

A third iontophoresis test with a volunteer was conducted with morphine hydrochloride in a concentration of 10 mg/ml for a period of 120 minutes. The results of the blood studies are represented by Line C in FIG. 4. The AUC is 5632 ng-min/ml, and the pH after 120 minutes of iontophoresis had only fallen to about 5.5. This insignificant decrease in pH value can be explained by depletion of silver available for the reaction. Nevertheless, this decrease was insufficient to cause any burns at the iontophoresis site.

While the example of morphine hydrochloride is set forth in specificity above, it will be appreciated that a variety of drugs can be successfully administered using the iontophoresis techniques of the present invention. The present invention is particularly adaptable to medicaments which are in the hydrochloride form, which includes a substantial number of therapeutically useful medicaments.

It will be readily appreciated that the present invention provides for improved control of the amount of medicament delivered. By varying the current flow, the time of iontophoresis, and the concentration of the medicament in the iontophoresis solution, the amount of the medicament administered to the patient can be controlled and quantified.

While most systems for the administration of medicaments will be aqueous based, that does not mean that the medicament medium must be in liquid form. The medicament can be incorporated into a gel (such as gelatin), a hydrogel, a gum (such as locust gum), a foam, or a nonionic cream (such as an oil-in-water emulsion cream having a nonionic surfactant) so as to make the iontophoresis process convenient. Moreover, in the case of narcotics, the incorporation of the medicament into a cream or gel minimizes the possibility of the drug being improperly extracted from electrode and misused. Furthermore, the system is also readily adaptable to use with local anesthetics, and similar substances, such as lidocaine hydrochloride.

E. Examples

The following examples are given to illustrate the general scope of the present invention, but these examples are not intended to limit the scope of the invention.

EXAMPLE 1

An iontophoresis procedure within the scope of the present invention was performed for the purpose of administering morphine to a human patient. The morphine was in the form of morphine hydrochloride in an aqueous solution having a concentration of about 10 mg/ml. This medicament solution was placed between a positive silver electrode and a vertical surface of the skin on the arm of a patient, and a negative electrode was placed on the opposing side of the arm of the patient. Iontophoresis was performed at a current of 2 mA for a period of thirty minutes.

During iontophoresis, the voltage at the interface between the silver electrode and the morphine hydrochloride solution was monitored and maintained below 1 V vs. Ag/AgCl electrode, i.e., below 1.23 V vs. SHE. During the iontophoresis process, an observable silver chloride precipitate was formed.

After the thirty minute period of iontophoresis, the pH of the iontophoresis solution had not appreciably changed from its initial value of about 6.1.

The physiological reactions typically observed in the administration of morphine were demonstrated by the patient. These reactions included dizziness, sleepiness, decreased pupil size, sluggishness in pupil reaction, and a slower reaction time. Under the electrode, there was a histamine wheal and a red flare which indicated transport of the morphine through the skin; however, no burning of the skin was observed. Free morphine levels measured in the serum by radioimmunoassay technique indicated an increase in morphine concentration and correlated with the time of iontophoresis.

EXAMPLE 2

An iontophoresis procedure within the scope of the present invention was performed according to the conditions and parameters of Example 1, except that the morphine hydrochloride was iontophoresed at 2 mA for a period of sixty minutes. The initial pH of the iontophoresis solution was about 6.1; after iontophoresis, the pH was about 5.5.

The physiological reactions typically observed in the administration of morphine were demonstrated by the patient, including dizziness, sleepiness, decreased pupil size, sluggishness in pupil reaction, and a slower reaction time. Under the electrode, there was a histamine wheal and a red flare which indicated transport of the morphine through the skin; however, no burning of the skin was observed. Free morphine levels measured in the serum by radioimmunoassay technique indicated an increase in morphine concentration and correlated with the time of iontophoresis.

EXAMPLE 3

An iontophoresis procedure within the scope of the present invention of Example 1 was performed according to the conditions and parameters of Example 1, except that the morphine hydrochloride was iontophoresed at 2 mA for a period of ninety minutes. The initial pH of the iontophoresis solution was about 6.1; after iontophoresis, the pH was about 6.0.

The physiological reactions typically observed in the administration of morphine were readily demonstrated. These reactions included dizziness, sleepiness, decreased pupil size, sluggishness in pupil reaction, and a slower reaction time. Under the electrode, there was a histamine wheal and a red flare which indicated transport of the morphine through the skin; however, no burning of the skin was observed. Free morphine levels measured in the serum by radioimmunoassay technique indicated an increase in morphine concentration and correlated with the time of iontophoresis.

EXAMPLE 4

An iontophoresis procedure within the scope of the present invention was performed according to the conditions and parameters of Example 1, except that the morphine hydrochloride was iontophoresed at 2 mA for a period of two hours. The initial pH of the iontophoresis solution was about 6.1; after iontophoresis, the pH was about 5.5.

The physiological reactions typically observed in the administration of morphine were readily demonstrated. These reactions included dizziness, sleepiness, decreased pupil size, sluggishness in pupil reaction, and a slower reaction time. Under the electrode, there was a histamine wheal and a red flare which indicated transport of the morphine through the skin; however, no burning of the skin was observed. Free morphine levels measured in the serum by radioimmunoassay technique indicated an increase in morphine concentration and correlated with the time of iontophoresis.

EXAMPLE 5

According to the iontophoresis procedures of this example, a reactive silver metal electrode was used for the purpose of administering Dilaudid to a patient by iontophoresis. The drug, hydromorphone hydrochloride, was in an aqueous solution having a concentration of about 2 mg/ml. This medicament solution was placed between the positive silver electrode and one surface of the skin on the arm of a patient, and a negative electrode was placed on the opposing side of the arm of the patient. Iontophoresis was allowed to occur at a current of about 0.5 mA for thirty minutes.

During iontophoresis, the voltage at the interface of the silver electrode and the medicament solution was monitored and maintained below 1 V (vs. Ag/AgCl electrode), which would be less than the electrolysis voltage of water at that electrode. During iontophoresis, the formation of a silver chloride precipitate was observed.

After a period of thirty minutes of iontophoresis, it was observed that the pH of the medicament solution had not appreciably changed.

The physiological reactions typically observed in the administration of Dilaudid were demonstrated by the patient, including dizziness, sleepiness, decreased pupil size, sluggishness in pupil reaction, and a slower reaction time. Under the electrode, there was a histamine wheal (with an elevation of about 1 to 3 mm) and a red flare which indicated transport of the hydromorphone hydrochloride through the skin; however, no burning of the skin was observed.

EXAMPLE 6

An iontophoresis procedure within the scope of the present invention was performed according to the conditions and parameters of Example 5, except that the hydromorphone hydrochloride was embedded in cream and placed in contact with the skin of the patient and a silver electrode.

The physiological reactions typically observed in the administration of Dilaudid were demonstrated by the patient, including dizziness, sleepiness, decreased pupil size, sluggishness in pupil reaction, and a slower reaction time. Under the electrode, there was a histamine wheal and a red flare which indicated transport of the hydromorphone hydrochloride through the skin; however, no burning of the skin was observed.

EXAMPLE 7

An iontophoresis procedure within the scope of the present invention is performed according to the conditions and parameters of Example 5, except that the hydromorphone hydrochloride is iontophoresed at 2 mA for a period of ninety minutes.

The physiological reactions typically observed in the administration of Dilaudid are readily demonstratable. These reactions include dizziness, sleepiness, decreased pupil size, sluggishness in pupil reaction, and a slower reaction time. Under the electrode, there is a histamine wheal and a red flare which indicate transport of the hydromorphone through the skin; however, no burning of the skin is observed.

EXAMPLE 8

An iontophoresis procedure within the scope of the present invention was performed according to the conditions and parameters of Example 5, except that the hydromorphone hydrochloride was iontophoresed at 2 mA for a period of two hours.

The physiological reactions typically observed in the administration of Dilaudid were readily demonstrated. These reactions included dizziness, sleepiness, decreased pupil size, sluggishness in pupil reaction, and a slower reaction time. Under the electrode, there was a histamine wheal and a red flare which indicated transport of the hydromorphone through the skin; however, no burning of the skin was observed.

EXAMPLE 9

An iontophoresis procedure within the scope of the present invention was performed according to the conditions and parameters of Example 5, except that the hydromorphone hydrochloride in the medium adjacent the positive silver electrode was dispersed in a nonionic cream in a concentration of about 5 mg/ml. The cream was a cold cream-type oil-in-water, nonionic emulsion. Iontophoresis was conducted for 25 minutes with a current of 1 mA from the positive electrode.

The physiological reactions typically observed in the administration of Dilaudid were demonstrated by the patient, including dizziness, sleepiness, decreased pupil size, sluggishness in pupil reaction, and a slower reaction time. No substantial change in the pH of the medicament medium was observed during iontophoresis, and no burning to the skin of the patient resulted.

EXAMPLE 10

An iontophoresis procedure within the scope of the present invention is conducted according to the procedure of Example 9, except that iontophoresis is conducted for a period of two hours at a current of 1 mA for 25 minutes.

The physiological reactions typically observed in the administration of Dilaudid are demonstrable by the patient, including dizziness, sleepiness, decreased pupil size, sluggishness in pupil reaction, and a slower reaction time. No substantial change in the pH of the medicament medium is observed during iontophoresis, and no burning to the skin of the patient results.

EXAMPLE 11

An iontophoresis process within the scope of the present invention was performed in order to administer morphine to a patient. The medicament was in the form of morphine hydrochloride in an aqueous solution in gelatin having a concentration of 10 mg/ml. The morphine hydrochloride was combined with gelatin dissolved in distilled water; the solution was "set" into a cylindrical mold.

Iontophoresis was conducted with a reactive, positive silver electrode according to the conditions and parameters of Example 1, except that the procedure continued for sixty minutes.

The physiological reactions typically observed in the administration of morphine were demonstrated by the patient, including dizziness, sleepiness, decreased pupil size, sluggishness in pupil reaction, and a slower reaction time. No substantial change in the pH of the medicament medium was observed during iontophoresis, and no burning to the skin of the patient resulted.

EXAMPLE 12

An iontophoresis procedure within the scope of the present invention is used for the administration of morphine to a patient wherein the morphine is in the form of morphine sulfate in an aqueous solution having a concentration of 10 mg/ml. A positive lead electrode is utilized, and the current of 2 mA passes from the positive electrode for a period of thirty minutes. During iontophoresis, the negative sulfate ion (the complementary ion) reacts with the lead electrode to form an insoluble precipitate of lead sulfate. The positive morphine ion is transported through the medicament medium and through the skin of the patient.

The physiological reactions typically observed in the administration of morphine are demonstratable by the patient, including dizziness, sleepiness, decreased pupil size, sluggishness in pupil reaction, and a slower reaction time. No substantial change in the pH of the medicament medium is observed during iontophoresis, and no burning to the skin of the patient results.

EXAMPLE 13

An iontophoresis process within the scope of the present invention is conducted using a silver electrode for the purpose of administering magnesium to the patient for the treatment of certain cardiovascular conditions. The iontophoresis process is utilized because of the difficulty of absorption of magnesium through the gastro-intestinal tract.

The medicament is in the form of magnesium chloride in aqueous solution having a concentration of 200 mg/ml. Iontophoresis is applied from the positive electrode at a current of 2 mA for a period of 60 minutes.

During iontophoresis, the chloride ion (which results from the dissociation of magnesium chloride) reacts with the silver metal electrode to form a silver chloride precipitate on the surface of the positive silver electrode. The magnesium ion is transferred through the medium and through the skin of the patient.

F. Summary

In summary, the present invention makes it possible to maintain pH at safe levels during the iontophoresis procedure. Moreover, the reactive electrode removes potentially competing ions (which are produced by the reaction of complementary ions with the electrode in the iontophoresis solution) from solution as iontophoresis progresses, by reacting with the complementary ions to produce an insoluble precipitate.

Voltage at the interface of the metal electrode and the medicament medium can, according to the present invention, be maintained at approximately constant or slowly increasing levels as long as the necessary reactants are available, i.e., as long as the medicament is available for transport and the complementary ion and the electrode are available to react. The direct result of the reactive electrode is that the voltage at the interface of the electrode and the medicament medium can be maintained below the voltage necessary to result in the electrolysis reaction of water. Thus, since no H+ or OH− ions are produced, no extremes in pH result, and there are no pH-induced burns to the patient. Moreover, since no H+ and OH− ions are produced and the formation of competing ions is minimized, the amount of medicament transported through the skin is more closely proportional to the current flow during iontophoresis and can be more accurately quantified.

The invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by U.S. Letters Patent is:

1. A method for iontophoretically administering a medicament through the skin of a patient while minimizing the formation of competing ions in the medicament medium, the method comprising the steps of:
   (a) obtaining a first electrode comprised of silver and a second electrode;
   (b) obtaining a medicament dissolved in an aqueous medium so as to form medicament ions and complementary ions, said complementary ions being chloride ions capable of reacting with the first electrode to form an insoluble silver chloride precipitate;
   (c) placing the first electrode in communication with the medicament medium;
   (d) placing the medicament medium in communication with the patient such that the medium is disposed between the first electrode and the skin of the patient;
   (e) placing the second electrode in communication with the skin of the patient at a point separated from the first electrode;
   (f) creating an electrical voltage difference between the first and second electrodes, said voltage difference transporting the medicament ions through the skin of the patient, said voltage difference causing a reaction which results in the formation of a silver chloride precipitate by the reaction of the complementary ion with the first electrode, thereby avoiding formation of additional ions which would compete for charge transport with the medicament ions and reduce the amount of medicament administered to the patient; and
   maintaining a voltage at the interface of the first electrode and the medicament medium below a voltage at which electrolysis of the water in the aqueous medicament medium can occur.

2. A method for iontophoretically administering a medicament as defined in claim 1 wherein the first electrode is the anode and wherein the voltage at the interface between the first electrode and the medicament medium is maintained below about 1.23 volts versus a Standard Hydrogen Electrode.

3. A method for iontophoretically administering a medicament as defined in claim 1 wherein the first electrode is the cathode and wherein the voltage at the interface between the first electrode and the medicament medium is maintained below about 0.83 volts versus a Standard Hydrogen Electrode.

4. A method for iontophoretically administering a medicament as defined in claim 1 wherein the medicament medium comprises a gel containing the medicament ions.

5. A method for iontophoretically administering a medicament as defined in claim 1 wherein the medicament medium comprises a hydrogel containing the medicament ions.

6. A method for iontophoretically administering a medicament as defined in claim 1 wherein the medicament medium comprises a cream containing the medicament ions.

7. A method for iontophoretically administering a medicament as defined in claim 1 wherein the medicament medium comprises a gum containing the medicament ions.

8. A method for iontophoretically administering a medicament as defined in claim 1 wherein the medicament medium comprises a foam containing the medicament ions.

9. A method for iontophoretically administering a medicament as defined in claim 1 wherein the step of maintaining the voltage at the interface of the first electrode and the medicament medium below the voltage at which electrolysis of the medium can occur comprises the steps of:
   monitoring the voltage at the interface of the first electrode and the medicament medium by a separate sensing electrode; and
   controlling the voltage at the interface of the first electrode and the medicament medium in response to the voltage monitored thereat.

10. A method for iontophoretically administering a medicament as defined in claim 9 wherein the voltage at the interface of the first electrode and the medicament medium is controlled by terminating the current flow at the first electrode as the voltage at said interface approaches the voltage at which electrolysis of the medium can occur.

11. A method for iontophoretically administering a medicament as defined in claim 1, wherein the medicament medium comprises a gel containing the medicament ions.

12. A method for iontophoretically administering a medicament as defined in claim 1 wherein the medicament medium comprises a hydrogel containing the medicament ions.

13. A method for iontophoretically administering a medicament as defined in claim 1 wherein the medicament medium comprises a cream containing the medicament ions.

14. A method for iontophoretically administering a medicament as defined in claim 1 wherein the medicament medium comprises a gum containing the medicament ions.

15. A method for iontophoretically administering a medicament as defined in claim 1 wherein the medicament medium comprises a foam containing the medicament ions.

16. A method for iontophoretically administering a medicament as defined in claim 1 wherein the first electrode is the anode and wherein the voltage at the interface of the first electrode and the medicament medium is maintained below about 1.23 volts versus a Standard Hydrogen Electrode.

17. A method for iontophoretically administering a medicament as defined in claim 1 wherein the first electrode is the cathode and wherein the voltage at the interface between the first electrode and the medicament medium is maintained below about 0.83 volts versus a Standard Hydrogen Electrode.

18. A method for iontophoretically administering a medicament through the skin of a patient while controlling the pH in the medicament medium, the method comprising the steps of:
   (a) obtaining a first electrode comprised of silver and a second electrode;
   (b) obtaining a medicament dissolved in an aqueous medium so as to form medicament ions and complementary ions, said complementary ions being chloride ions capable of reacting with the first electrode to form an insoluble silver chloride precipitate;
   (c) placing the first electrode in communication with the medicament medium;
   (d) placing the medicament medium in communication with the patient such that the medium is disposed between the first electrode and the skin of the patient;
   (e) placing the second electrode in communication with the skin of the patient at a point separated from the first electrode;
   (f) creating an electrical voltage difference between the first and second electrodes, said voltage difference transporting the medicament ions through the skin of the patient, said voltage difference causing a reaction which results in the formation of an insoluble silver chloride precipitate from the reaction of the complementary ions with the first electrode; and
   (g) maintaining a voltage at the interface between the first electrode and the medicament medium below the electrolysis voltage of water, thereby preventing the formation of hydrogen and hydroxyl ions within the medium which would compete with the medicament ions to be transported through the skin of the patient and which would change the pH of the medicament solution.

19. A method for iontophoretically administering a medicament as defined in claim 18 wherein the step of maintaining the voltage at the interface of the first electrode and the medicament medium below the voltage at which electrolysis of the medium can occur comprises the steps of:
   monitoring the voltage at the interface of the first electrode and the medicament medium by a separate sensing electrode; and
   controlling the voltage at the interface of the first electrode and the medicament medium in response to the voltage monitored thereat.

20. A method for iontophoretically administering a medicament as defined in claim 19 wherein the voltage at the interface of the first electrode and the medicament medium is controlled by terminating the current flow at the first electrode as the voltage at said interface approaches the voltage at which electrolysis of the medium can occur.

21. A method for iontophoretically administering a medicament as defined in claim 18 wherein the first electrode is the anode and wherein the voltage at the interface between the first electrode and the medicament medium is maintained below about 1.23 volts versus a Standard Hydrogen Electrode.

22. A method for iontophoretically administering a medicament as defined in claim 18 wherein the first electrode is the cathode and wherein the voltage at the interface between the first electrode and the medicament medium is maintained below about 0.83 volts versus a Standard Hydrogen Electrode.

23. A method for iontophoretically administering a medicament as defined in claim 21 wherein the medicament is a narcotic.

24. A method for iontophoretically administering a medicament as defined in claim 23 wherein the medicament is selected from the group consisting of morphine, hydromorphone, oxymorphone, and methadone.

25. A method for iontophoretically administering a medicament as defined in claim 18 wherein the medicament is an anesthetic agent.

26. A method for iontophoretically administering a medicament as defined in claim 25 wherein the medicament is lidocaine hydrochloride.

27. A method for iontophoretically administering a medicament as defined in claim 18 wherein the medicament medium comprises a gel containing the medicament ions.

28. A method for iontophoretically administering a medicament as defined in claim 18 wherein the medicament medium comprises a hydrogel containing the medicament ions.

29. A method for iontophoretically administering a medicament as defined in claim 18 wherein the medicament medium comprises a cream containing the medicament ions.

30. A method for iontophoretically administering a medicament as defined in claim 18 wherein the medicament medium comprises a gum containing the medicament ions.

31. A method for iontophoretically administering a medicament as defined in claim 18 wherein the medicament medium comprises a foam containing the medicament ions.

32. An iontophoresis system for delivering a medicament to a patient comprising:
   an aqueous medicament solution including medicament ions and complementary ions, said complementary ions being chloride ions;
   a first electrode constructed of silver which is capable of reacting with the complementary chloride ion to form silver chloride which is insoluble in the medicament solution;
   means for placing the first electrode in communication with the aqueous medicament solution;
   means for placing the aqueous medicament solution in communication with a patient;
   means for placing a second electrode in communication with a patient at a point on said patient separated from said first electrode; and
   means for applying an electrical voltage difference between the first and second electrodes such that the medicament ions are transported to the patient, and such that the first electrode reacts with the complementary ions at a voltage below the electrolysis voltage of water.

33. An iontophoresis system for delivering a medicament to a patient by iontophoresis while controlling the pH in the medicament solution, comprising:
   a first electrode comprised of silver;

a second electrode;

an aqueous medicament solution including medicament ions and chloride ions, said solution being placed in communication with the first electrode;

means for placing the medicament solution in communication with a patient;

means for placing the second electrode in communication with a patient at a point on said patient separated from said first electrode and the means for placing the medicament solution in communication with the patient; and means for applying a voltage difference between the first and second electrodes sufficient to cause a reaction between the chloride ions of the medicament solution and the silver of the first electrode in order to form an insoluble silver chloride precipitate which maintains the voltage at the interface between the first electrode and the medicament solution below the electrolysis voltage of water.

34. An iontophoresis system for delivering a medicament to a patient as defined in claim 33 wherein said medicament ions are a narcotic.

35. An iontophoresis system for delivering a medicament as defined in claim 33 wherein the medicament solution comprises a gel containing the medicament ions.

36. An iontophoresis system for delivering a medicament as defined in claim 33 wherein the medicament solution comprises a hydrogel containing the medicament ions.

37. An iontophoresis system for delivering a medicament as defined in claim 33 wherein the medicament solution comprises a cream containing the medicament ions.

38. An iontophoresis system for delivering a medicament as defined in claim 33 wherein the medicament solution comprises a gum containing the medicament ions.

39. An iontophoresis system for delivering a medicament as defined in claim 33 wherein the medicament solution comprises a foam containing the medicament ions.

40. An iontophoresis system for delivering a medicament to a patient as defined in claim 33 further comprising means for determining when the voltage at the interface of the first electrode and the medicament solution exceeds the electrolysis voltage of water so that the iontophoretic process may be terminated before injury to the patient occurs, said means comprising a sensing electrode capable of monitoring the voltage at the interface of the first electrode and the medicament solution.

* * * * *

UNITED STATES PATENT AND TRADEMARK OFFICE
CERTIFICATE OF CORRECTION

PATENT NO.   :   4,752,285
DATED        :   June 21, 1988
INVENTOR(S)  :   Tomasz J. Petelenz et al.

It is certified that error appears in the above-identified patent and that said Letters Patent is hereby corrected as shown below:

Abstract, line 10, "skin of patient" should be --skin of a patient--
Column 4, line 10, "iontopheretic" should be --iontophoretic--
Column 7, line 11, "maybe" should be --may be--
Column 8, line 13, "fully manifest" should be --fully manifested--

Signed and Sealed this

Fourteenth Day of March, 1989

*Attest:*

DONALD J. QUIGG

*Attesting Officer*        *Commissioner of Patents and Trademarks*

REEXAMINATION CERTIFICATE (2658th)
United States Patent [19]
Petelenz et al.

[11] B1 4,752,285
[45] Certificate Issued Aug. 22, 1995

[54] METHODS AND APPARATUS FOR IONTOPHORESIS APPLICATION OF MEDICAMENTS

[75] Inventors: Tomasz J. Petelenz; Robert L. Stephen; Stephen C. Jacobsen, all of Salt Lake City, Utah

[73] Assignee: The University of Utah Research Foundation, Salt Lake City, Utah

Reexamination Requests:
No. 90/001,744, Apr. 5, 1989
No. 90/003,116, Jul. 6, 1993

Reexamination Certificate for:
Patent No.: 4,752,285
Issued: Jun. 21, 1988
Appl. No.: 841,329
Filed: Mar. 19, 1986

Certificate of Correction issued Mar. 14, 1989.

[51] Int. Cl.⁶ .............................................. A61N 1/30
[52] U.S. Cl. .......................................... 604/20; 607/75
[58] Field of Search ................. 604/20, 891, 892, 896, 604/897, 890.1, 20, 21, 65; 128/798, 799, 802, 803; 607/75, 149–152

[56] References Cited
U.S. PATENT DOCUMENTS

| | | |
|---|---|---|
| 3,289,671 | 12/1966 | Troutman et al. |
| 3,834,373 | 9/1974 | Sato .................................... 2.06/128 |
| 3,991,755 | 11/1976 | Vernon et al. |
| 4,215,696 | 8/1980 | Bremer et al. |
| 4,292,968 | 10/1981 | Ellis. |
| 4,383,529 | 5/1983 | Webster ................................ 604/20 |
| 4,474,570 | 10/1984 | Ariura et al. ........................ 604/20 |
| 4,526,176 | 7/1985 | Bremer et al. |
| 4,570,637 | 2/1986 | Gomes et al. |
| 4,602,909 | 7/1986 | Csillik et al. ........................ 604/20 |
| 4,731,049 | 3/1988 | Parsi ...................................... 604/20 |
| 4,744,787 | 5/1988 | Phipps et al. ........................ 604/20 |
| 4,747,819 | 5/1988 | Phipps et al. ........................ 604/20 |

FOREIGN PATENT DOCUMENTS

| | | |
|---|---|---|
| 80303620 | 6/1984 | European Pat. Off. ............ 4/5 |
| 0171742 | 2/1986 | European Pat. Off. . |
| 0182520 | 5/1986 | European Pat. Off. . |
| 0195643 | 9/1986 | European Pat. Off. . |
| 2246037 | 9/1972 | Germany . |
| 2116037 | 9/1983 | United Kingdom . |

OTHER PUBLICATIONS

Shereff, Richard H et al., "Effect of Beta Adrenergic Stimulation and Blockage on Immediate Hypersensitivity Skin Test Reactions", J. Allergy Clin. Immunol., Dec. 1973, vol. 52, No. 6, pp. 328–333.

Arvidsson, S. B. et al., "Painless Venipuncture—A Clinical Trial of Iontophoresis of Lidocaine for Venipuncture in Blood Donors," Acta Anaesthesiologica Scandinavica, Apr. 1984, vol. 28 pp. 209–210.

(List continued on next page.)

*Primary Examiner*—C. Fred Rosembaum

[57] ABSTRACT

Methods and apparatus for administering known quantities of medicaments by iontophoresis while avoiding burns caused by extremes in the pH of the medicament medium during passage of an electric current are disclosed. It has been found that, as iontophoresis progresses in conventional iontophoresis systems, the electrolysis of water occurs to produce hydrogen or hydroxyl ions at the interface of the electrode and medicament medium. Since these ions are highly mobile, they are transported directly into the skin of a patient in preference to the larger medicament ions. Thus, extreme changes in pH are experienced which result in burns due to the acidification or alkalinization of the medicament medium and passage of electric current through the skin. The present invention also avoids the production of other competing ions by employing a reactive electrode. The electrode and the medicament are chosen such that the electrode will react with the complementary ion (the ion which forms upon the dissociation of the medicament in solution) to form an insoluble material.

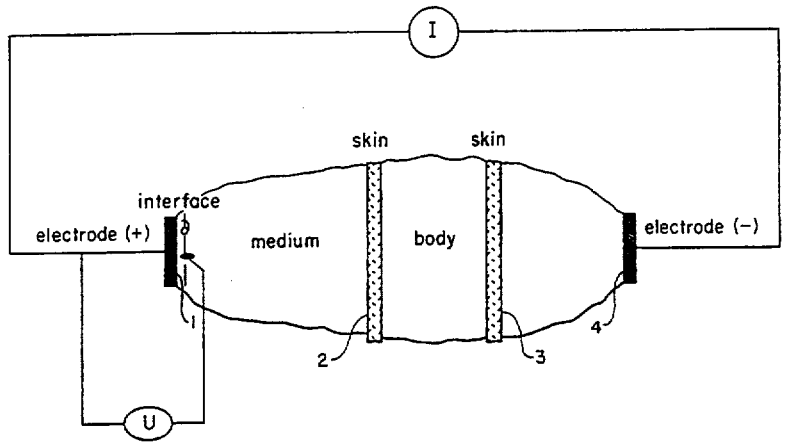

OTHER PUBLICATIONS

Samarin et al, "Physiochemical Study of Iontophoresis", Voprosy Kutrortologii, Fizioterapii Lechebnio Fizicheskoi Kul'tury, 1957, No. 4 pp. 3–7.

Rebinder, P. A., "Iontophoresis, in Electrokinetischeski Kapillarnykh system"; monographiceskiy sbornik. USSR Academy of Science, 1956 pp. 310–327.

Rossi, G. A. et al., Bulletin—Italian Society of Experimental Biology, Chemical Abstracts, vol. 99 pp. 806–812.

Abstract "Iontophoresis as a Potential Method of Insulin Administration", T. J Petelenz et al., International Symposium on Artificial Organs, Biomedical Engineering and Transplantation, Jan. 20–23, 1986, Salt Lake City, Utah.

Abstract "Evaluation of Transdermal Iontophoretic Drug Delivery", J. B. Phipps et al, International Symposium on Artificial Organs, Biomedical Engineering and Transplantation, Jan. 20–23, 1986, Salt Lake City, Utah.

Excerpt, "Corrosion and Corrosion Control", Third Edition, 1985, Uhlig et al., pp. 27–29.

Poster Presentation "Evaluation of Transdermal Iontophoretic Drug Delivery", J. B. Phipps et al, International Symposium on Artificial Organs, Biomedical Engineering and Transplantation, Jan. 20–23, 1986 Salt Lake City Utah.

Bird et al., "Iontophoretic Application of Opiates to the Locus Coeraleus", Brain Research 1977, 122 (3), 523–33 (Abstract).

Abramowitsch, et al., Treatment by Ion Transfer (Iontophoresis), Grune & Stratton, New York, pp. 1–54, 1946.

Girya, Research on the Protective Properties of Ion—Exchange Membranes During the Electrophoresis of Medicines, Problems of Health Resort Treatment and Physical Therapy in the Urals, Sverdlovsk, pp. 83–89, 1967.

Jones, et al., New Methods of Measuring the Rate of Aqueous Flow in Man with Fluorescein, Ertpl Eye Res. vol. 5, pp. 208–220, 1966.

Korstanje, et al., Iontophoresis, Pharmaceutisch Weekblad, vol. 117, pp. 1,184–1,188, 1982.

Levai, Dionin Iontophoresis by Means of Gelatin Plates, Munchner Medizinische Wochenschrift, No. 50, pp. 1,936–1, 937, 1934.

Rose, et al., Introduction to Techniques in Developmental Electrobiology, Developmental Biology, vol. 16, pp. 24–25, 1960.

Teorell, Transport Processes in Membranes in Relation of the Nerve Mechanism, Experimental Cell Research, Suppl. 5, pp. 83–100, 1959.

Vladimirov, et al., Nonpolarized Electrodes for the Iontophoresis of Penicillin, Collected Works of the V. M. Motolov State Medical Institute in Tomsk and the Tomsk Oblast Scientific Research Institute of Physical Medication and Health-Resort Treatment, vol. 8, pp. 186–192, 1953.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9, 10, 19-20 and 40 is confirmed.

Claims 1-8, 18, 21-39 are cancelled.

Claims 11-17 are determined to be patentable as amended.

New claims 41-66 are added and determined to be patentable.

11. A method for iontophoretically administering a medicament as defined in claim [1] *9*, wherein the medicament medium comprises a gel containing the medicament ions.

12. A method for iontophoretically administering a medicament as defined in claim [1] *9* wherein the medicament medium comprises a hydrogel containing the medicament ions.

13. A method for iontophoretically administering a medicament as defined in claim [1] *9* wherein the medicament medium comprises a cream containing the medicament ions.

14. A method for iontophoretically administering a medicament as defined in claim [1] *9* wherein the medicament medium comprises a gum containing the medicament ions.

15. A method for iontophoretically administering a medicament as defined in claim [1] *9* wherein the medicament medium comprises a foam containing the medicament ions.

16. A method for iontophoretically administering a medicament as defined in claim [1] *9* wherein the first electrode is the anode and wherein the voltage at the interface of the first electrode and the medicament medium is maintained below about 1.23 volts versus a Standard Hydrogen Electrode.

17. A method for iontophoretically administering a medicament as defined in claim [1] *9 wherein the first electrode is the cathode and wherein the voltage at the interface between the first electrode and the medicament medium is maintained below about 0.83 versus a Standard Hydrogen Electrode.*

*41. A method for iontophoretically administering a medicament as defined in claim 9 wherein the voltage at the interface of the first electrode and the medicament medium is controlled by regulating the current flow at the first electrode as the voltage at said interface approaches the voltage at which electrolysis of the medium can occur.*

*42. A method for iontophoretically administering a medicament as defined in claim 24 wherein the step of maintaining the voltage at the interface of the first electrode and the medicament medium below the voltage at which electrolysis of the medium can occur comprises the steps of:*

*monitoring the voltage at the interface of the first electrode and the medicament medium by a separate sensing electrode; and*

*controlling the voltage at the interface of the first electrode and the medicament medium in response to the voltage monitored thereat.*

*43. A method for iontophoretically administering a medicament as defined in claim 42 wherein the voltage at the interface of the first electrode and the medicament medium is controlled by terminating the current flow at the first electrode as the voltage at said interface approaches the voltage at which electrolysis of the medium can occur.*

*44. A method for iontophoretically administering a medicament as defined in claim 42 wherein the medicament medium comprises a gel containing the medicament ions.*

*45. A method for iontophoretically administering a medicament as defined in claim 42 wherein the medicament medium comprises a hydrogel containing the medicament ions.*

*46. A method for iontophoretically administering a medicament as defined in claim 42 wherein the medicament medium comprises a cream comprising the medicament ions.*

*47. A method for iontophoretically administering a medicament as defined in claim 42 wherein the medicament medium comprises a gum containing the medicament ions.*

*48. A method for iontophoretically administering a medicament as defined in claim 42 wherein the medicament medium comprises a foam containing the medicament ions.*

*49. A method for iontophoretically administering a medicament as defined in claim 19 wherein the first electrode is the anode and wherein the voltage at the interface between the first electrode and the medicament medium is maintained below about 1.23 volts versus a Standard Hydrogen Electrode.*

*50. A method for iontophoretically administering a medicament as defined in claim 49 wherein the medicament is a narcotic.*

*51. A method for iontophoretically administering a medicament as defined in claim 50 wherein the medicament is selected from the group consisting of morphine, hydromorphone, oxymorphone, and methadone.*

*52. A method for iontophoretically administering a medicament as defined in claim 19 wherein the first electrode is the cathode and wherein the voltage at the interface between the first electrode and the medicament medium is maintained below about 0.83 volts versus a Standard Hydrogen Electrode.*

*53. A method for iontophoretically administering a medicament as defined in claim 19 wherein the medicament is an anesthetic agent.*

*54. A method for iontophoretically administering a medicament as defined in claim 53 wherein the medicament is lidocaine hydrochloride.*

*55. A method for iontophoretically administering a medicament as defined in claim 19 wherein the medicament medium comprises a gel containing the medicament ions.*

*56. A method for iontophoretically administering a medicament as defined in claim 19 wherein the medicament medium comprises a hydrogel containing the medicament ions.*

*57. A method for iontophoretically administering a medicament as defined in claim 19 wherein the medicament medium comprises a cream containing the medicament ions.*

58. A method for iontophoretically administering a medicament as defined in claim 19 wherein the medicament medium comprises a gum containing the medicament ions.

59. A method for iontophoretically administering a medicament as defined in claim 19 wherein the medicament medium comprises a foam containing the medicament ions.

60. An iontophoresis system for delivering a medicament to a patient as defined in claim 40 wherein said medicament ions are a narcotic.

61. An iontophoresis system for delivering a medicament to a patient as defined in claim 40 wherein the medicament solution comprises a gel containing the medicament ions.

62. An iontophoresis system for delivering a medicament to a patient as defined in claim 40 wherein the medicament solution comprises a hydrogel containing the medicament ions.

63. An iontophoresis system for delivering a medicament to a patient as defined in claim 40 wherein the medicament solution comprises a cream containing the medicament ions.

64. An iontophoresis system for delivering a medicament to a patient as defined in claim 40 wherein the medicament solution comprises a gum comprising the medicament ions.

65. An iontophoresis system for delivering a medicament to a patient as defined in claim 40 wherein the medicament solution comprises a foam containing the medicament ions.

66. An iontophoresis system for delivering a medicament to a patient while controlling pH in the medicament solution as defined in claim 33 further comprising means for determining when the voltage at the interface of the first electrode and the medicament solution exceeds the electrolysis voltage of water so that the iontophoretic process may be regulated before injury to the patient occurs, said means comprising a sensing electrode capable of monitoring the voltage at the interface of the first electrode and the medicament solution.

* * * * *